United States Patent
Boulot

(10) Patent No.: US 10,531,898 B2
(45) Date of Patent: Jan. 14, 2020

(54) SACROILIAC FIXATION IMPLANTAT FOR AN INTERVERTEBRAL LINKING ROD

(71) Applicant: ORTHOPAEDIC & SPINE DEVELOPMENT (OSD), Avignon (FR)

(72) Inventor: Jacques Boulot, Toulouse (FR)

(73) Assignee: ORTHOPAEDIC & SPINE DEVELOPMENT (OSD), Avignon (FR)

( * ) Notice: Subject to any disclaimer, the term of this patent is extended or adjusted under 35 U.S.C. 154(b) by 1 day.

(21) Appl. No.: 15/738,818

(22) PCT Filed: Jun. 30, 2016

(86) PCT No.: PCT/FR2016/051649
§ 371 (c)(1),
(2) Date: Dec. 21, 2017

(87) PCT Pub. No.: WO2017/006028
PCT Pub. Date: Jan. 12, 2017

(65) Prior Publication Data
US 2018/0177535 A1 Jun. 28, 2018

(30) Foreign Application Priority Data
Jul. 3, 2015 (FR) ...................................... 15 56338

(51) Int. Cl.
*A61B 17/70* (2006.01)
*A61B 17/86* (2006.01)
(52) U.S. Cl.
CPC ...... *A61B 17/7058* (2013.01); *A61B 17/7055* (2013.01); *A61B 17/86* (2013.01)

(58) Field of Classification Search
CPC ............ A61B 17/7043; A61B 17/7044; A61B 17/7049; A61B 17/7052; A61B 17/7055; A61B 17/7058; A61B 17/8066
See application file for complete search history.

(56) References Cited

U.S. PATENT DOCUMENTS

| 5,133,717 A | 7/1992 | Chopin |
| 2008/0021454 A1 | 1/2008 | Chao et al. |

(Continued)

FOREIGN PATENT DOCUMENTS

| WO | 94/20048 A1 | 9/1994 |
| WO | 2012/104794 A1 | 8/2012 |

(Continued)

OTHER PUBLICATIONS

Aug. 31, 2016 International Search Report issued in International Patent Application No. PCT/FR2016/051649.

*Primary Examiner* — Julianna N Harvey
*Assistant Examiner* — Christina Negrellirodriguez
(74) *Attorney, Agent, or Firm* — Oliff PLC

(57) ABSTRACT

A sacroiliac fixation implant comprising a one-piece anchoring component supporting a connecting element of the linking rod and provided with three orifices for the passage of anchoring screws, where the anchoring component comprises: an elongated main wall in which are formed two orifices, where the connecting element is interposed between the two orifices; and a secondary wall protruding from the main wall at the level of one end so that the anchoring component has a general «L» shape, a third orifice being formed on said secondary wall; wherein each orifice is internally delimited by a spherical shaped bearing face extended by a truncated-cone shaped flared face centered on a central axis, and wherein the orientations of the central axes and the taper angles of the flared faces are shaped so as (Continued)

to enable an arrangement of the screwing axes of the three anchoring screws.

14 Claims, 7 Drawing Sheets

(56) References Cited

U.S. PATENT DOCUMENTS

2012/0022595 A1* 1/2012 Pham ................ A61B 17/7055
                                                    606/278
2015/0105828 A1    4/2015 Reckling et al.

FOREIGN PATENT DOCUMENTS

| WO | 2013/153482 A1 | 10/2013 |
| WO | 2014/146018 A1 | 9/2014 |

* cited by examiner

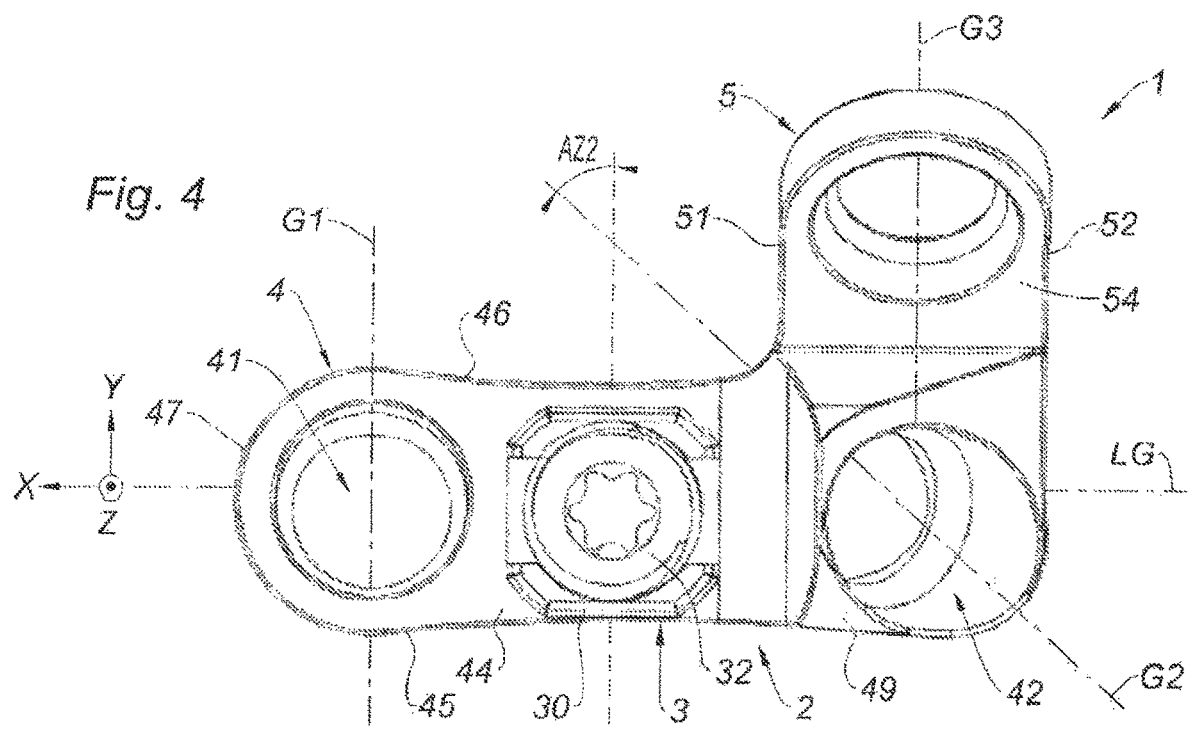
Fig. 4
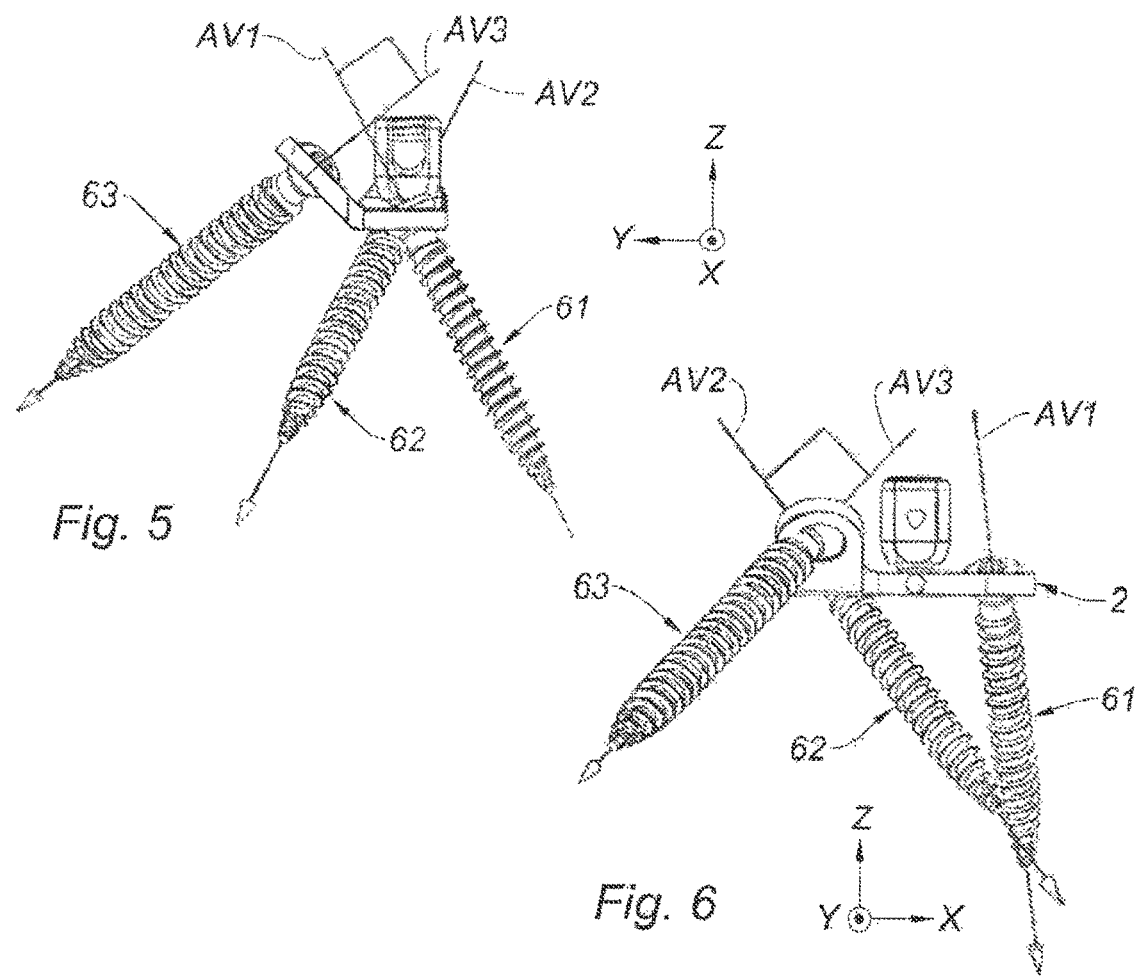
Fig. 5
Fig. 6

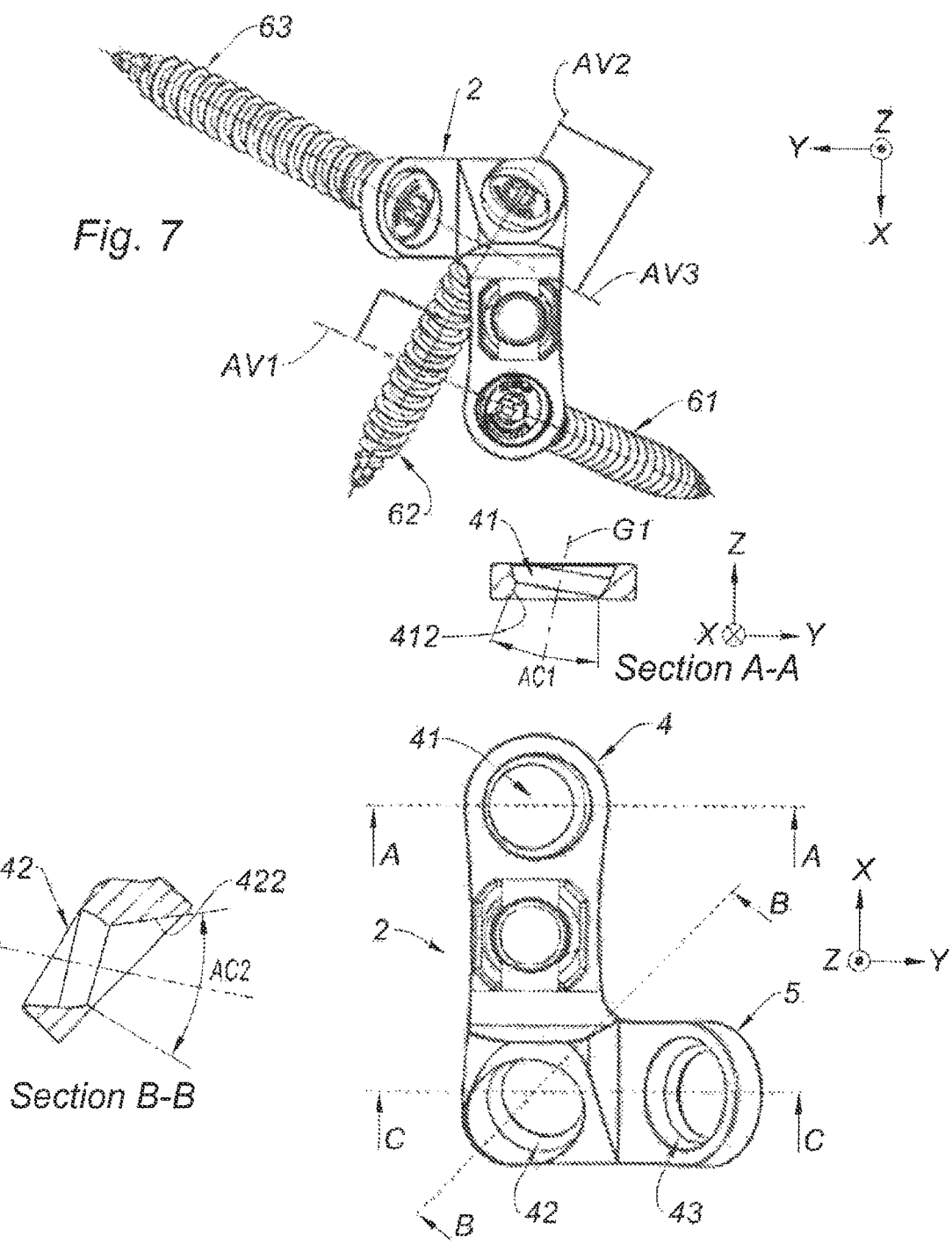

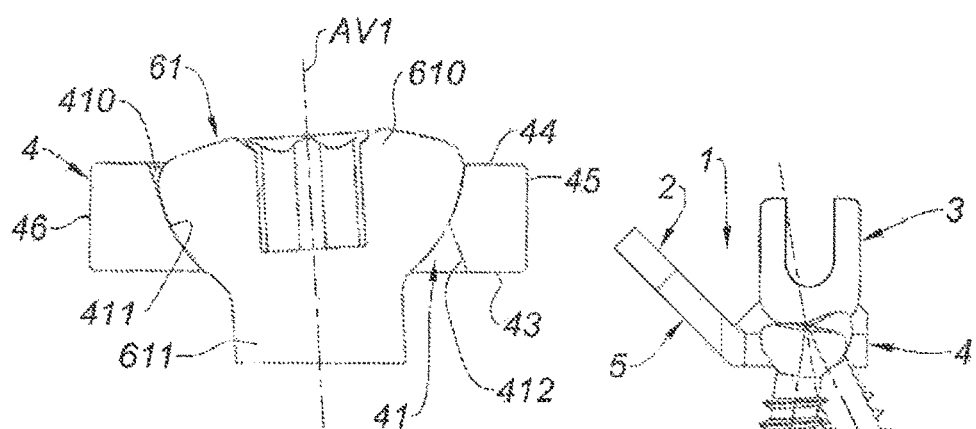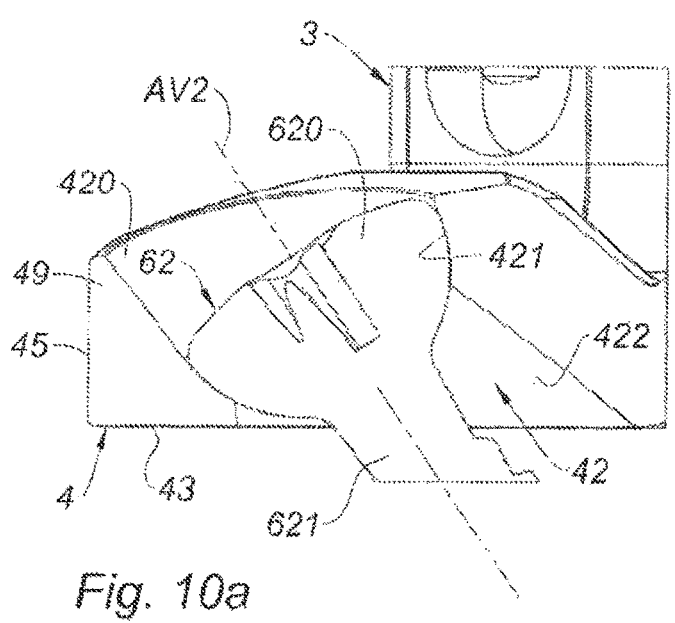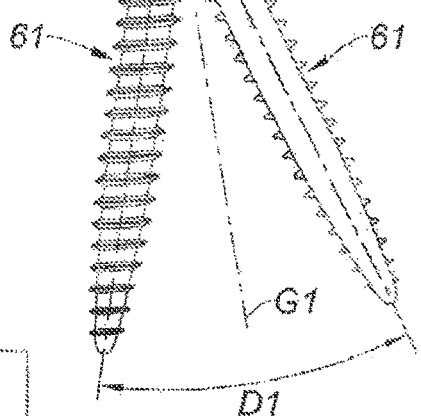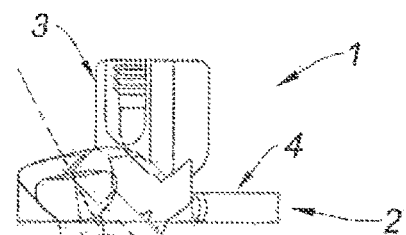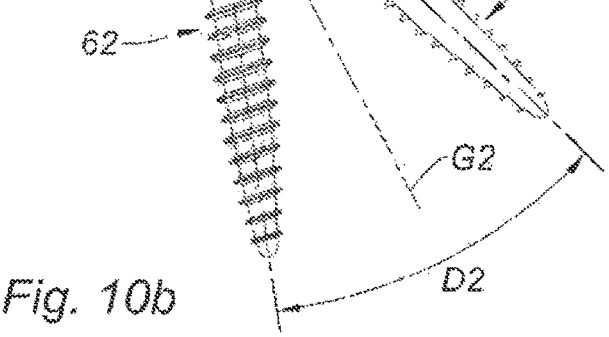
Fig. 9a
Fig. 9b
Fig. 10a
Fig. 10b

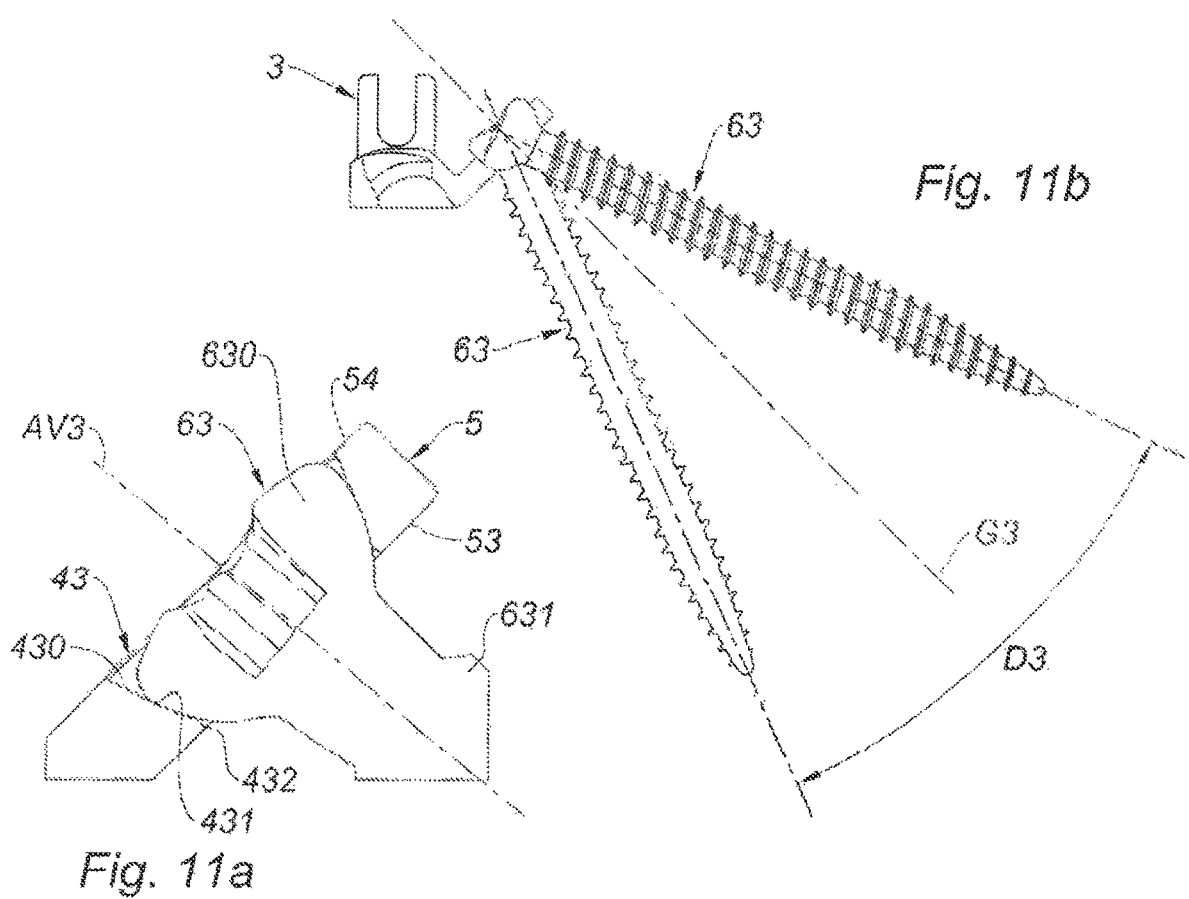
Fig. 11b
Fig. 11a
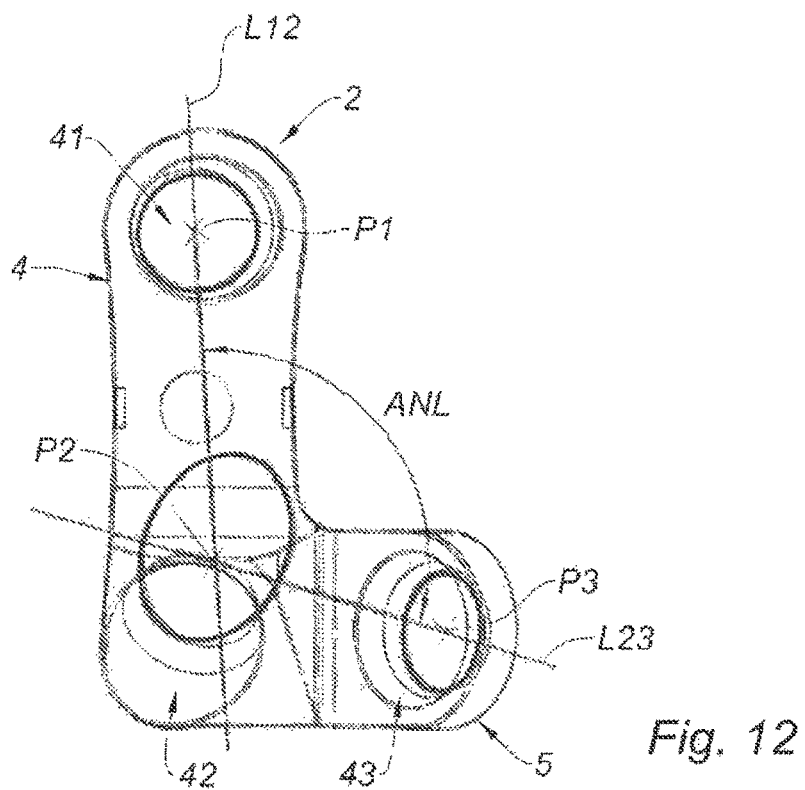
Fig. 12

SACROILIAC FIXATION IMPLANTAT FOR AN INTERVERTEBRAL LINKING ROD

FIELD

The present invention relates to a sacroiliac fixation implant for an intervertebral linking rod.

The invention falls within the field of vertebral osteosynthesis materials intended to correct the deformations of the vertebral column, and in particular of the lumbar spine.

BACKGROUND

In this field of vertebral osteosynthesis, the correction or the immobilization of a portion of a vertebral column is achieved by means of several fixation implants (sometimes called connectors or anchoring plates) capable of cooperating with bone anchoring screws (or pedicular screws) and of rigidly connecting together rigid linking rods, in order to achieve the anchorage of these linking rods to the vertebrae.

In the case of the treatment of the lumbar spine, it is known to ensure an anchorage of the rigid linking rods on the sacrum, and even on both the sacrum and the hip bone. In this respect, it is necessary to use a fixation implant called sacroiliac fixation implant capable of cooperating with screws for anchoring on the sacrum (called sacral anchoring screws) and with a screw for anchoring on the hip bone (called iliac anchoring screw).

However, the forces subjected to the sacral and iliac anchoring screws require a particularly strong bone anchorage in the region of the sacrum in order to be able to resist the detachment of the screws and of the implants out of the bone.

It is known from the document WO 2013/153482 to propose a sacroiliac fixation implant composed of a sacral anchoring plate with two orifices for the passage of two sacral anchoring screws, a sacral connecting part intended to be mounted on one of the two orifices of the sacral anchoring plate and having a hole for the engagement of a linking rod, means for assembling the connecting part to the sacral anchoring plate, an iliac anchoring plate intended to be mounted on the other one of the two orifices of the sacral anchoring plate and having a hole for the passage of an iliac anchoring screw, as well as tightening screws.

The drawback of such an implant lies essentially in its complexity, multiplying the number of parts to assemble together (sacral anchoring plate, sacral connecting part, iliac anchoring plate, nuts and assembly means), such a multiplication of assemblies also contributing in increasing the dimensions, and especially the thickness or the overall height of the implant, and also in significantly increasing the time of the surgical intervention, not to mention the possible complications that this can entail.

It is also known from the document U.S. Pat. No. 5,133,717 to propose, in an embodiment illustrated in its FIG. 2, a sacroiliac fixation implant composed of a plate provided with three orifices for the passage of sacral anchoring screws and of an iliac anchoring screw, with a slotted boss provided with a threaded orifice for tightening a linking rod. Although this implant is somehow compact, it does not offer an optimum orientation for the anchoring screws which would allow for a sufficient and durable anchorage.

SUMMARY

The present invention aims at solving all or part of these problems by proposing an implant with a simple design, offering an orientation of the anchoring screws which allows for an optimum and durable anchorage on the sacrum and on the hip bone, while being relatively compact.

To this end, it proposes a sacroiliac fixation implant for an intervertebral linking rod, said implant comprising a one-piece anchoring component supporting a connecting element for the linking rod and provided with three orifices including a first orifice for the passage of a first sacral anchoring screw, a second orifice for the passage of a second sacral anchoring screw, and a third orifice for the passage of an iliac anchoring screw, said implant being remarkable in that:

a) the anchoring component comprises:

a main wall elongated according to a longitudinal direction and having a lower face and an opposite upper face as well as opposite first and second longitudinal edges, wherein the first orifice is formed at a first end of said main wall and the second orifice is formed at a second end of said main wall, and wherein the connecting element is mounted protruding from and secured on the upper face of the main wall and is interposed between the first orifice and the second orifice; and a secondary wall protruding from the second longitudinal edge of the main wall at the level of its second end, so that the anchoring component has a general «L» shape, said secondary wall having a lower face and an opposite upper face, wherein the third orifice is formed on said secondary wall;

b) each orifice is at least delimited internally and successively, from the upper face in the direction of the lower face of the concerned main wall or secondary wall, by an inlet face being a cylindrical or conical portion, extended by a bearing face being a spherical portion in turn extended by a flared face being a truncated-cone portion with a predefined taper angle and which widens as it gets closer to the lower face, wherein the inlet face, the bearing face and the flared face together form a smooth surface of revolution centered around a common central axis, including a first central axis associated to the first orifice, a second central axis associated to the second orifice and a third central axis associated to the third orifice;

c) the main wall has, on the one hand, a thickened portion at the level of the second end and, on the other hand, a less thick portion between the first end and the thickened portion, wherein the thickened portion forms a raised step with respect to the less thick portion and the second orifice is formed in this thickened portion, and wherein the first orifice is formed in this less thick portion and the connecting element is provided on this less thick portion;

d) the orientations of said three central axes and the taper angles of said three flared faces are shaped so as to enable at least one arrangement of the screwing axes of the three anchoring screws according to a three-orthogonal trihedron, with the screwing axis of the first sacral anchoring screw orthogonal to the screwing axis of the second sacral anchoring screw and to the screwing axis of the iliac anchoring screw, and with the screwing axis of the second sacral anchoring screw orthogonal to the screwing axis of the iliac anchoring screw.

Thus, the three orifices have central axes and truncated-cone portions such that the three anchoring screws, once in place with their degrees of freedom enabled by the spherical and truncated-cone portions, are enabled to extend according to their respective screwing axes which will form a three-orthogonal trihedron and will together confer an enhanced and durable anchorage.

Indeed, the anchorage according to three directions (screwing axes) orthogonal to each other results in that none of the three anchoring screws is tensioned according to its own screwing axis, that is to say that it does not tend to be pulled out when tension forces are exerted on the implant via the intervertebral linking rod. The three anchoring screws not being displaced when loaded, this results in a better primary fixation of the implant and the risk of loosening due to the forces of the movements of the patient is reduced to zero.

Moreover, thanks to this optimization of the orientations of the central axes of the orifices, the implant may be reduced in its dimensions because it is not necessary to provide for complementary assembly or reinforcement means, thereby justifying the use of a one-piece anchoring component with an «L» shaped geometry optimized in terms of compactness and mechanical strength.

Finally, the spherical shapes of the bearing faces of the orifices of the anchoring component will allow offering polyaxial bearings of the anchoring screws, in other words bearings with the possibility of multidirectional inclination of the anchoring screws with respect to the anchoring part, in order to enable the practitioner or the surgeon to adapt to the different morphologies of the patients, and to not necessarily comply exactly to the orientation of the screwing axes according to a three-orthogonal trihedron; the taperings of the flared faces of the orifices enabling the multidirectional angular displacements of the anchoring screws within predefined limits. In other words, thanks to the invention, it is possible to be set in the arrangement of the screwing axes of the three anchoring screws according to a three-orthogonal trihedron, but also in arrangements where the screwing axes are away from the three-orthogonal trihedron arrangement within the limit of the angular displacements enabled by the flared faces of the orifices.

It should be noted that the «L» shape of the part has the advantage of contributing to the compactness and to the mechanical strength of the implant, in perfect match with the anchorage stresses imposed by the anchoring screws. The lower faces of the main and secondary walls form faces for bearing on the skeleton, and in particular on the sacrum and on the hip bone. These lower faces may be smooth or still have elements for gripping on the skeleton, in other words they may have a surface roughness offering a controlled roughness in order to promote the bone gripping; such gripping elements may be for example in the form of teeth or tips.

In addition, the presence of the thickened portion actually allows controlling the desired orientation of the central axis of the second orifice, while addressing a congestion problem. Indeed, this thickened portion forms a bulge which allows forming and orientating the second orifice, so as to allow a properly chosen orientation for the second sacral screw, and the less thick portion offers a reduced thickness while accommodating the connecting element which will be free to be displaced angularly.

It should also be noted that the surfaces of revolution of the three orifices, which are necessarily smooth, enable, after screwing of the three anchoring screws in the sacrum and the hip bone, rotations of these anchoring screws on the spherical shaped bearing faces in order to allow preserving the disjoint movements of the sacrum and of the hip bone which are possible thanks to the sacroiliac joint, thanks to the cooperation between the heads of the anchoring screws and these bearing faces; each of these anchoring screws having a spherical shaped bearing surface which bears on the bearing face of the concerned orifice.

Finally, it should be noted that, thanks to this implant according to the invention, only three screwing actions of the anchoring screws are sufficient to ensure the final fixation of the implant, thereby allowing reducing the intervention time for setting such an implant.

According to one feature, the connecting element comprises a fastener cooperating with a tightening member for tightening the linking rod on said fastener, where said fastener is pivotally mounted on a ball joint secured to the anchoring component so that said fastener has three rotational degrees of freedom on said ball joint.

In this manner, the fastener has a freedom of orientation which allows compensating for a possible misalignment of the intervertebral linking rod.

Advantageously, the fastener has a fall movability, relative to the ball joint and to the main wall, inscribed within a cone centered on this ball joint and with an apex angle larger than or equal to 40 degrees, and preferably comprised between 45 and 65 degrees.

Thanks to the conformation of the main wall, it is indeed possible to obtain such a movability of the fastener, in order to accurately fit to the arrangement of the intervertebral linking rod.

According to another feature, the secondary wall is inclined upward with respect to the main wall with an inclination comprised between 30 and 60 degrees, preferably between 40 and 50 degrees.

This inclination of the secondary wall which rises with respect to the main wall (in other words which defines a slope inclined upward when associating the top to the upper face and when associating the bottom to the lower face), offers a geometry particularly adapted for a three-orthogonal anchorage of the anchoring screws, and an optimum placement of the iliac anchoring screw on the hip bone.

Advantageously, the lower face of the secondary wall lies in the continuity of the lower face of the secondary wall with an inclination comprised between 30 and 60 degrees, preferably between 40 and 50 degrees.

According to another feature, considering a first point corresponding to the intersection between the first central axis and the plane of the lower face of the main wall, a second point corresponding to the intersection between the second central axis and the plane of the lower face of the main wall, and a third point corresponding to the intersection between the third central axis and the plane of the lower face of the secondary wall, and considering a first line passing through the first point and through the second point, and a second line passing through the third point and the second point, said first line and said second line intersect on the second point at an angle comprised between 100 and 120 degrees, and preferably between 105 and 115 degrees.

These orientations of the two lines also participate in the optimization of the orientation of the anchoring screws in order to make the anchorage on the sacrum and the hip bone reliable.

According to another feature, the first orifice and the second orifice are shaped so that:
the first central axis is orientated, in an orientation direction extending from the upper face toward the lower face of the main wall, in the direction of the first longitudinal edge of the main wall; and
the second central axis is orientated, in an orientation direction extending from the upper face toward the lower face of the main wall, in the direction of the second longitudinal edge of the main wall and toward the first orifice.

Thus, the first sacral anchoring screw will be implanted according to a direction called radial-front direction, whereas the second sacral anchoring screw will be implanted according to a direction called outer-front direction.

In a particular embodiment, the secondary wall has opposite first transverse edge and second transverse edge, where the first transverse edge is closer to the first end of the main wall than the second transverse edge, and the third axis is orientated, in an orientation direction extending from the upper face toward the lower face of the secondary wall, in the direction of the second transverse edge and opposite to the main wall.

Thus, the iliac anchoring screw will be implanted in the hip bone according to a completely external direction, orthogonally to the first and second sacral anchoring screws.

Advantageously, considering an orthonormal frame composed of a longitudinal axis (X) parallel to the longitudinal direction and orientated from the second orifice toward the first orifice, a transverse axis (Y) orthogonal to the longitudinal axis where the longitudinal axis and the transverse axis define a plane (X, Y) parallel to the lower face of the main wall and where said transverse axis (Y) is orientated from the first longitudinal edge toward the second longitudinal edge, and a vertical axis (Z) orthogonal to the lower face of the main wall and orientated from the lower face toward the upper face, at least one of the following geometric conditions is satisfied:

- the first central axis has an angle with the vertical axis (Z) in the plane (Y, Z) comprised between +5 and +15 degrees, and in particular between +8 and +12 degrees;
- the first central axis has an angle with the vertical axis (Z) in the plane (X, Z) comprised between −5 and +5 degrees, and in particular between −2 and +2 degrees;
- the first central axis has an angle with the transverse axis (Y) in the plane (X, Y) comprised between −5 and +5 degrees, and in particular between −2 and +2 degrees;
- the second central axis has an angle with the vertical axis (Z) in the plane (Y, Z) comprised between −15 and −25 degrees, and in particular between −18 and −22 degrees;
- the second central axis has an angle with the vertical axis (Z) in the plane (X, Z) comprised between −18 and −28 degrees, and in particular between −21 and −25 degrees;
- the second central axis has an angle with the transverse axis (Y) in the plane (X, Y) comprised between +37 and +47 degrees, and in particular between +40 and +44 degrees;
- the third central axis has an angle with the vertical axis (Z) in the plane (Y, Z) comprised between −40 and −50 degrees, and in particular between −43 and −47 degrees;
- the third central axis has an angle with the vertical axis (Z) in the plane (X, Z) comprised between −5 and +5 degrees, and in particular between −2 and +2 degrees;
- the third central axis has an angle with the transverse axis (Y) in the plane (Y, Z) comprised between −5 and +5 degrees, and in particular between −2 and +2 degrees.

These geometric conditions also participate in the optimization of the orientation of the anchoring screws in order to make the anchorage on the sacrum and the hip bone reliable.

In a particular embodiment, the main wall has, according to the longitudinal direction, a length comprised between 35 and 50 millimeter, preferably between 38 and 42 millimeter, a width considered between its two longitudinal edges comprised between 10 and 15 millimeter, and a thickness considered between its lower face and its upper face comprised between 2.5 and 4.5 millimeter, preferably between 3.2 and 3.8 millimeter.

Thus, the dimensions are adapted to the anatomy of the sacroiliac region, while offering a compactness, and especially a small height or thickness, which will allow facilitating the positioning of the linking rod in the connecting element.

According to a possibility of the invention, the anchoring component has an overall height, considered according to a vertical axis (Z) orthogonal to the lower face of the main wall, comprised between 13 and 17 millimeter, preferably between 14 and 16 millimeter.

According to a possibility of the invention, the truncated-cone shaped flared face of each orifice has a taper angle comprised between 20 and 50 degrees.

Advantageously, the taper angle for the first orifice is comprised between 20 and 25 degrees, the taper angle for the second orifice is comprised between 40 and 50 degrees, and the taper angle for the third orifice is comprised between 35 and 45 degrees.

These taper angles have been optimized to allow an improved reliability of the anchorage.

Advantageously, the less thick portion of the main wall has a thickness which is constant and smaller than the thickness of the thickened portion.

Thus, the connecting element is provided on this less thick portion, where the thickness is constant, in order to promote a wide angular displacement of the connecting element, while allowing having an implant with the smallest possible thickness.

According to a possibility, the secondary wall extends this thickened portion of the main wall transversely, according to a transverse direction orthogonal to the longitudinal direction of the main wall.

The invention also relates to a sacroiliac fixation system for an intervertebral linking rod, said system comprising an implant in accordance with the invention, and three anchoring screws comprising a first sacral anchoring screw engaged in the first orifice of the anchoring part, a second anchoring screw engaged in the second orifice of the anchoring component and an iliac anchoring screw engaged in the third orifice of the anchoring part, each anchoring screw having a threaded rod extended by a head having a spherical shaped bearing surface, where said bearing curt ace bears directly and polyaxially on the bearing face of the corresponding orifice, where the orientations of the three central axes and the taper angles of the flared faces of the three orifices enable an arrangement of the screwing axes of the three anchoring screws according to a three-orthogonal trihedron, with the screwing axis of the first sacral anchoring screw orthogonal to the screwing axis of the second sacral anchoring screw and to the screwing axis of the iliac anchoring screw, and with the screwing axis of the second sacral anchoring screw orthogonal to the screwing axis of the iliac anchoring screw.

BRIEF DESCRIPTION OF THE DRAWINGS

Other features and advantages of the present invention will appear upon reading the detailed description hereinafter, of a non-limiting embodiment, made with reference to the appended figures in which:

FIGS. 2 to 4 are respectively schematic side, front and top views of the implant of FIG. 1;

FIGS. 5 to 7 are respectively schematic side, front and top views of the implant of FIG. 1, with the anchoring screws in place on the implant and with the screwing axes of the anchoring screws schematized to illustrate the perpendicularities between the screwing axes;

FIG. 8 is a schematic top view of the implant of FIG. 1 with three sectional views according to the section axes A-A, B-B and C-C;

FIGS. 9a and 9b are schematic views of the implant of FIG. 1 according to a section plane in the first orifice and with the first sacral anchoring screw in position, respectively with an enlarged view on the first orifice (FIG. 9a) and an enlarged view showing the enabled angular displacement of the first sacral anchoring screw inside the first orifice (FIG. 9b);

FIGS. 10a and 10b are schematic views of the implant of FIG. 1 according to a section plane in the second orifice with the second sacral anchoring screw in position, respectively with an enlarged view on the second orifice (FIG. 10a) and an enlarged view showing the enabled angular displacement of the second sacral anchoring screw inside the second orifice (FIG. 10b);

FIGS. 11a and 11b are schematic views of the implant of FIG. 1 according to a section plane in the third orifice with the iliac anchoring screw in position, respectively with an enlarged view on the third orifice (FIG. 11a) and an enlarged view showing the enabled angular displacement of the iliac anchoring screw inside the third orifice (FIG. 11b);

FIG. 12 is a schematic top view of the implant of FIG. 1 illustrating a first line and a second line;

DESCRIPTION

Figure 1:
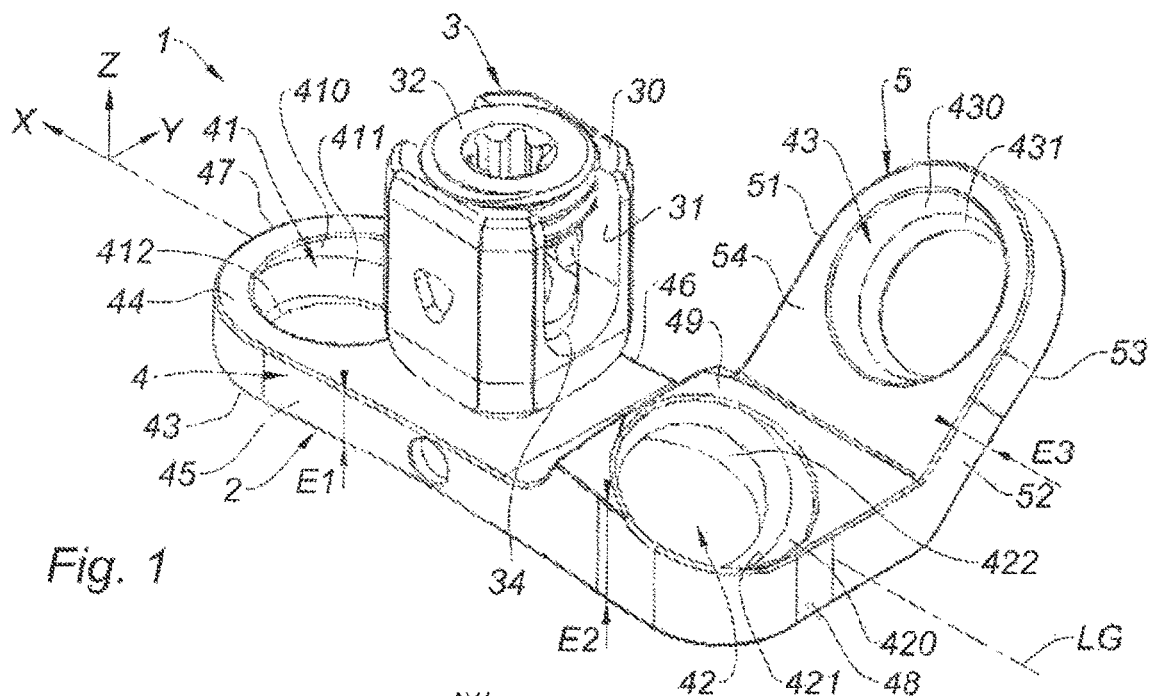
FIG. 1 is a schematic perspective view of a sacroiliac fixation implant in accordance with the invention.

Referring to the figures, a sacroiliac fixation implant 1 comprises an anchoring component 2 supporting a connecting element 3 for an intervertebral linking rod (not illustrated).

The anchoring component 2 is formed by a one-piece component, in other words is made integrally in a biocompatible material, such as for example a titanium alloy, and possibly with a surface treatment or coating.

The Anchoring Component 2 Includes:
- a main wall 4 in which are formed a first orifice 41 for the passage of a first sacral anchoring screw 61 and a second orifice 42 for the passage of a second sacral anchoring screw 62; and
- a secondary wall 5 in which is formed a third orifice 50 for the passage of an iliac anchoring screw 63.

The main wall 4 is elongated according to a longitudinal direction LG and has a lower face 43 and an opposite upper face 44 as well as opposite first and second longitudinal edges 45, 46, wherein the first orifice 41 is formed at a first end 47 of the main wall 4 and the second orifice 42 is formed at a second end 48 of the main wall 4.

The first and second longitudinal edges 45, 46 are substantially parallel to the longitudinal direction of the main wall 4. The first longitudinal edge 45 is intended to extend at the internal side of the sacrum SAC, whereas the second longitudinal edge 46 is intended to extend at the external side of the sacrum SAC (facing the hip bone OIL).

The main wall 4 has, according to the longitudinal direction LG, a length comprised between 35 and 50 millimeter, preferably between 38 and 42 millimeter, and has a width considered between its two longitudinal edges 45, 46 comprised between 10 and 15 millimeter.

The first end 47 is intended to be positioned at the upper side of the sacrum SAC (facing the vertebral column COV), whereas the second end 48 is intended to be positioned at the lower side of the sacrum SAC (facing the coccyx), Thus, it is necessary to have two symmetrical implants, with a left implant 1 right implant 1; all figures illustrating a right implant 1 as example.

The lower face 43 is intended to bear on the sacrum SAC, whereas the upper face 44 is intended to be opposite to the sacrum SAC (facing the intervertebral linking rod). The lower face 43 may be smooth or have elements (teeth or tips) for anchoring on the sacrum SAC, in other words, it may have a surface roughness offering a controlled roughness in order to promote the bone gripping, In turn, the connecting element 3 is positioned on the upper face 44 of the main wall 4, between the first orifice 41 and the second orifice 42.

This Connecting Element 3 Comprises:
- a fastener 30 generally shaped as a slotted ring, where the slot 31 has at its upper portion an internal thread capable of cooperating with a tightening screw 32 for tightening the linking rod (not illustrated) on the fastener 30;
- a ball joint 33 (shown in a dashed line in FIG. 2) secured (in particular by welding) to the upper face 44 of the main wall 4, where the fastener 30 is pivotally mounted on this ball joint 33 so that this fastener 30 has three rotational degrees of freedom on the ball joint 33; and
- an insert 34 disposed inside the fastener 30 and having a lower face to hemispherically bearing on the ball joint 33 and an arcuate upper face capable of receiving the linking rod.

When in place, the linking rod (not illustrated) crosses the fastener 30 by passing through the slot 31, while bearing on the insert 34, and the linking rod is tightened between this insert 34 and the tightening screw 32.

Figure 13A:
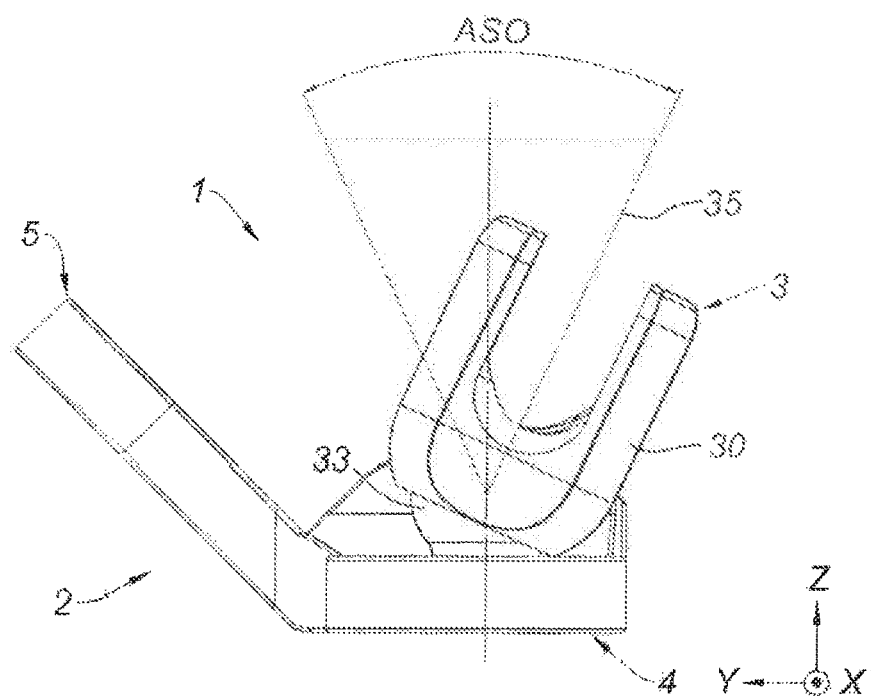
FIGS. 13a and 13b are respectively side and front schematic views of the implant of FIG. 1, illustrating the angular displacement cone of the fastener of the connecting element.
Figure 13B:
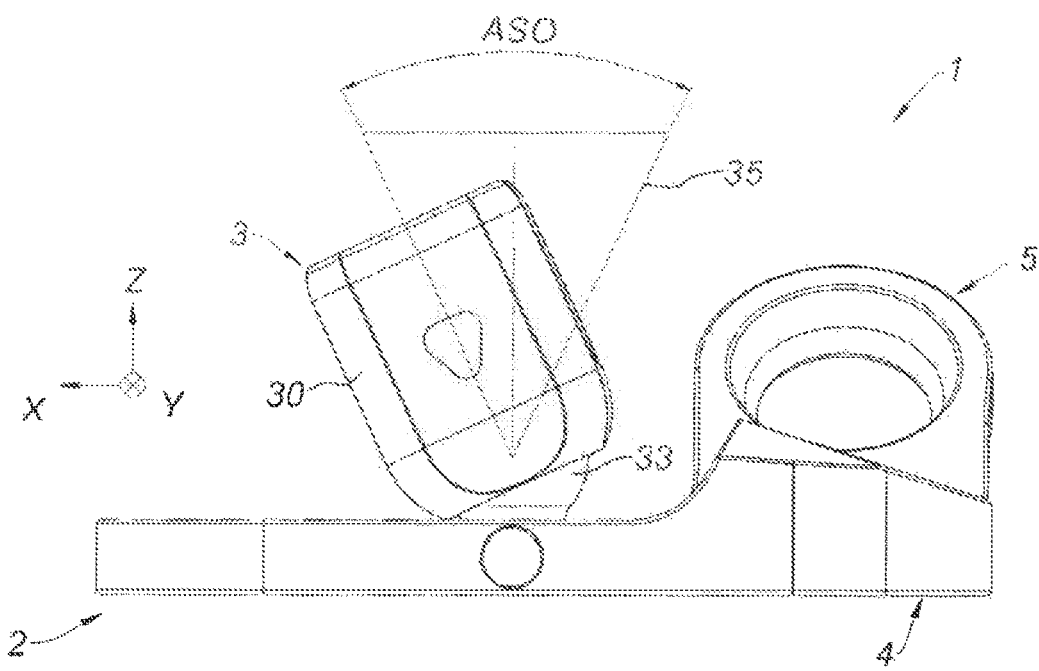

As shown in FIGS. 13a and 13b, in particular because of the implantation of the connecting element 3 on a planar portion of the upper face 44 of the main wall 4, the fastener 30 has a full movability, relative to the ball joint 33 and to the main wall 4, which is inscribed within a cone 35 centered on this ball joint 33 and with an apex angle ASO larger than or equal to 40 degrees, and in particular in the range of 50 degree.

Figure 2:
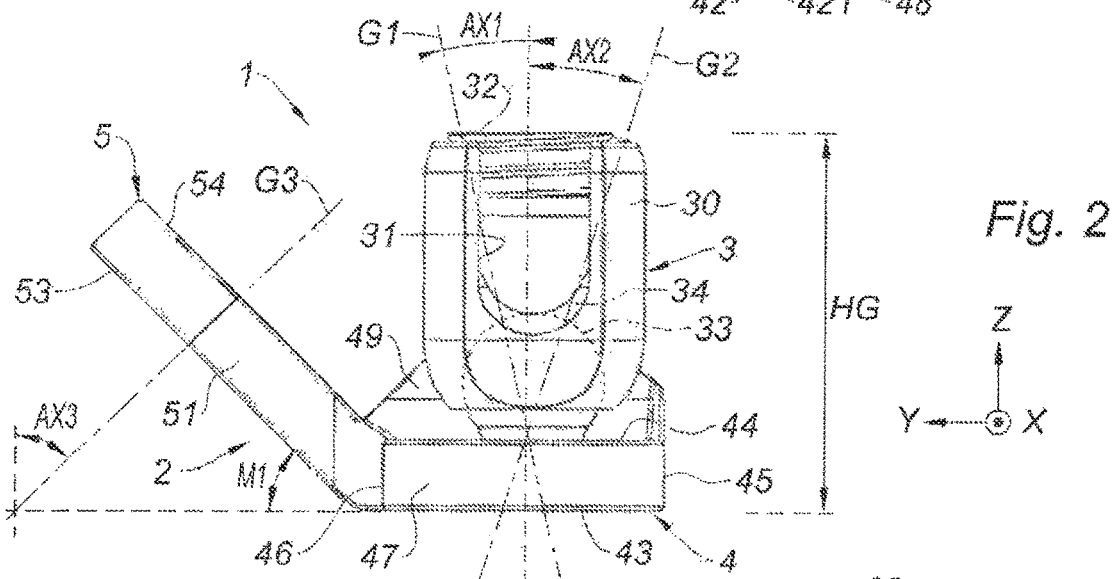

The anchoring component has an overall height HG, considered according to a vertical axis Z orthogonal to the lower face 43 of the main wall 4, comprised between 13 and 17 millimeter, preferably between 14 and 16 millimeter; this overall height HG being shown in FIG. 2 and measured between the lower face 43 and the apex of the fastener 30.

The main wall 4 has a thickened portion 49 at the level of the second end 48, which thus forms a raised step, and the second orifice 42 is formed in this thickened portion 49. In turn, the first orifice 41 and the connecting element 3 are positioned on the less thick portion. Thus, the main wall 4 has, between the first end 47 and the thickened portion 49, this less thick portion whose thickness E1 is constant, whereas the thickened portion 49 has a thickness E2 greater than the thickness E1.

As example, the less thick portion has a thickness E1 comprised between 2.5 and 3.5 millimeter, and the thickened portion 49 has a thickness E2 greater by about 1.0 to 2.0 millimeter than the thickness E1, and therefore the thickness E2 is comprised between 3.5 and 4.5 millimeter.

In the following description, we will define an orthonormal frame defined by three axes:

an axis X called longitudinal axis parallel to the longitudinal direction of the main wall and orientated from the second orifice 42 toward the first orifice 41 (in other words from the second end 48 toward the first end 47), this longitudinal axis X being, when anchored on a patient, substantially parallel to the vertebral column and therefore to the intervertebral linking rod and orientated from the bottom of the sacrum SAC toward the top of the sacrum SAC;

an axis Y called transverse axis orthogonal to the longitudinal axis X and orientated from the first longitudinal edge 45 toward the second longitudinal edge 46. Where the longitudinal axis X and the transverse axis Y define a plane (X, Y) substantially parallel to the lower face 43 of the main wall 4, this transverse axis Y extending, when anchored on a patient, transversely between the right and left hip bones OIL and being orientated from the internal side of the sacrum SAC toward the external side of the sacrum SAC, in other words toward the hip bone OIL concerned by the anchorage of the implant 1;

an axis Z called vertical axis orthogonal to the plane (X, Y), and therefore substantially orthogonal to the lower face 43 of the main wall 4, and orientated from the lower face 43 toward the upper face 44, this vertical axis Z being, when anchored on a patient, substantially perpendicular to the anchorage area of the implant 1 on the sacrum SAC and orientated from the sacrum SAC outwardly from the patient.

The secondary wall 5 protrudes, substantially at a right angle, from the second longitudinal edge 46 of the main wall 4, at the level of the second end 48, so that the anchoring component 2 has a general «L» shape. More specifically, the secondary wall 5 extends the thickened portion 49 transversely, according to the transverse direction Y. The secondary wall 5 has a lower face 53 and an opposite upper face 54, where the lower face 53 extends the lower face 43 of the main wall 4 and the upper face 54 extends the upper face 44 of the main wall 4.

The secondary wall 5 is inclined upward at an angle M1 with respect to the main wall 4, forming a ramp which surpasses the upper face 44 of the main wall 4.

More specifically, the lower face 53 of the secondary wall 5 lies in the continuity of the lower face 43 of the secondary wall 4 with an inclination M1 comprised between 30 and 60 degrees, preferably between 40 and 50 degrees.

The secondary wall 5 has a thickness E3 substantially equivalent to the thickness E1, being also comprised between 2.5 and 3.5 millimeter.

The secondary wall 5 has opposite first transverse edge 51 and second transverse edge 52 substantially parallel to the transverse axis Y, where the first transverse edge 51 is closer to the first end 47 of the main wall 4 than the second transverse edge 52. In other words, the first transverse edge 51 is intended to be positioned at the upper side of the sacrum SAC (facing the vertebral column COY), whereas the second transverse edge 52 is intended to be positioned at the lower side of the sacrum SAC (facing the coccyx).

The following description covers the conformations with three orifices 41, 42, 50.

The first orifice 41 is delimited internally and successively from the top to the bottom (in other words from the upper face 44 in the direction of the lower face 43) by a cylindrical or conical shaped inlet face 410, extended by a spherical shaped bearing face 411 in turn extended by a truncated-cone shaped flared face 412 (flared in the sense that the flared face widens as it gets closer to the lower face 43), wherein these three faces 410, 411, 412 together form a surface of revolution centered around a first central axis G1; being obviously clear that this surface of the first orifice 41 is smooth and devoid of any internal thread.

Referring to the section A-A of FIG. 8, the taper angle AC1 of the flared face 412 of the first orifice 41 is in the range of 20 degrees.

Referring to FIGS. 9A and 913, the first sacral anchoring screw 61, extending according to a main axis AV1 called screwing axis, has a threaded rod 611 extended by a head 610 having a spherical shaped bearing surface, where this bearing surface bears directly and polyaxially on the bearing face 411 of the first orifice 41.

Because of the shape of the bearing face 411 and of the flared face 412, the first sacral anchoring screw 61 has, inside this first orifice 41, an angular displacement D1 in the range of 30 to 40 degrees between its two extreme positions, in other words the screwing axis AV1 of the first sacral anchoring screw 61 can evolve inside a cone with an angle D1 centered on the first central axis G1.

The first central axis G1 is orientated, in an orientation direction extending from the upper face 44 toward the lower face 43 of the main wall 4 (in other words, in an orientation direction corresponding to the direction of insertion of the first sacral anchoring screw 61), in the direction of the first longitudinal edge 45 of the main wall 4, as shown in FIG. 2.

Figure 3:
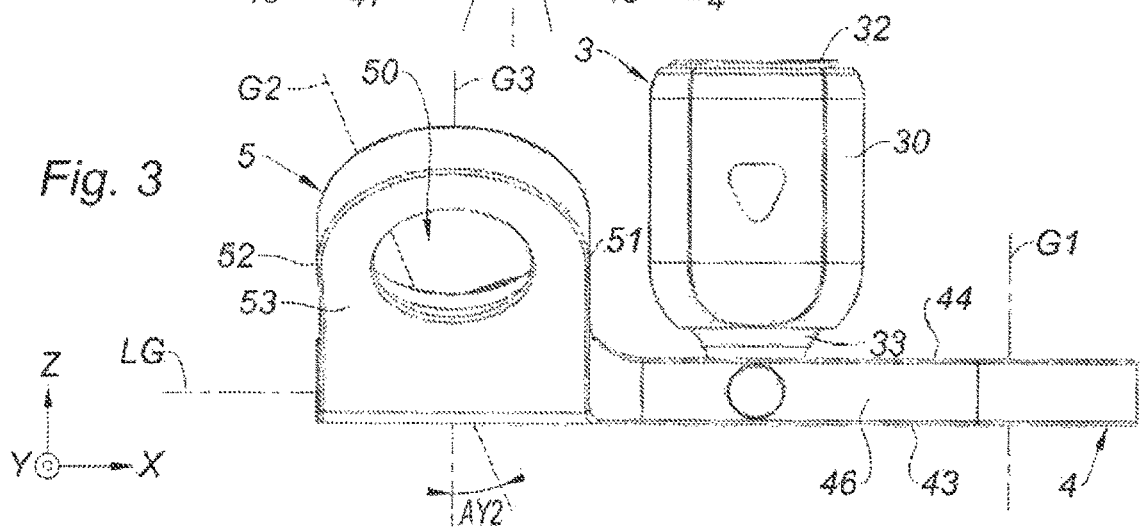

More specifically, this first central axis G1 satisfies the following geometric conditions;

as shown in FIG. 2, the first central axis G1 has an angle AX1 with the vertical axis (Z) in the plane (Y, Z) comprised between +5 and +15 degrees, and in particular between +8 and +12 degrees, this angle AX1 being +10 degrees in the example of FIG. 2;

as shown in FIG. 3, the first central axis G1 has an angle AY1 with the vertical axis (Z) in the plane (X, Z) comprised between −5 and +5 degrees, and in particular between −2 and +2 degrees, this angle AY1 being 0 degrees in the example of FIG. 3, so that this angle AY1 is not referenced;

as shown in FIG. 4, the first central axis G1 has an angle AZ1 with the transverse axis (Y) in the plane (X, Y) comprised between −5 and +5 degrees, and in particular between −2 and +2 degrees, this angle AZ1 being 0 degrees in the example of FIG. 4, so that this angle AZ1 is not referenced.

The second orifice 42 is delimited internally and successively from the top to the bottom (in other words from the upper face 44 in the direction of the lower face 43) by a cylindrical or conical shaped inlet face 420, extended by a spherical shaped bearing face 421 in turn extended by a truncated-cone shaped flared face 422 (flared in the sense that the flared face widens as it gets closer to the lower face 43), where these three faces 420, 421, 422 together form a surface of revolution centered around a second central axis G2; being obviously clear that this surface of the second orifice 42 is smooth and devoid of any internal thread.

Referring to the section B-B of FIG. 8, the taper angle AC2 of the flared face 422 of the second orifice 42 is in the range of 46 degrees.

Referring to FIGS. 10A and 10B, the second sacral anchoring screw 62, extending according to a main axis AV2 called screwing axis, has a threaded rod 621 extended by a head 620 having a spherical shaped bearing surface, where this bearing surface bears directly and polyaxially on the bearing face 421 of the second orifice 42.

Because of the shape of the bearing face 421 and of the flared face 422, the second sacral anchoring screw 62 has, inside this second orifice 42, an angular displacement D2 in the range of 35 to 45 degrees between its two extreme positions, in other words the screwing axis AV2 of the second sacral anchoring screw 62 can evolve inside a cone with an angle D2 centered on the second central axis G2.

The second central axis G2 is orientated, in an orientation direction extending from the upper face 44 toward the lower face 43 of the main wall 4 (in other words, in an orientation direction corresponding to the direction of insertion of the second sacral anchoring screw 62), in the direction of the second longitudinal edge 46 of the main wall 4, as shown in FIG. 2, and also in the direction of the first orifice 41, as shown in FIG. 4.

More specifically, this second central axis G2 satisfies the following geometric conditions:
- as shown in FIG. 2, the second central axis G2 has an angle AX2 with the vertical axis (Z) in the plane (Y, Z) comprised between −15 and −25 degrees, and in particular between −18 and −22 degrees, this angle AX2 being −20 degrees in the example of FIG. 2;
- as shown in FIG. 3, the second central axis G2 has an angle AY2 with the vertical axis (Z) in the plane (X, Z) comprised between −18 and −28 degrees, and in particular between −21 and −25 degrees, this angle AY2 being −23 degrees in the example of FIG. 3;
- as shown in FIG. 4, the second central axis G2 has an angle AZ2 with the transverse axis (Y) in the plane (X, Y) comprised between +37 and +47 degrees, and in particular between +40 and +44 degrees, this angle AZ2 being +42 degrees in the example of FIG. 4.

Moreover, and as shown in FIG. 12, considering a first point P1 corresponding to the intersection between the first central axis G1 and the plane of the lower face 43 of the main wall 4, a second point P2 corresponding to the intersection between the second central axis G2 and the plane of the lower face 43 of the main wall 4, and a third point P3 corresponding to the intersection between the third central axis G3 and the plane of the lower face 53 of the secondary wall 5, and considering a first line L12 passing through the first point P1 and through the second point P2, and a second line L23 passing through the third point P3 and the second point P2, this first line L12 and this second line L23 intersect on the second point P2 at an angle ANL in the range of 110 degrees.

The third orifice 43 is delimited internally and successively from the top to the bottom (in other words from the upper face 54 in the direction of the lower face 53) by a cylindrical or conical shaped inlet face 430, extended by a spherical shaped bearing face 431 in turn extended by a truncated-cone shaped flared face 432 (flared in the sense that the flared face widens as it gets closer to the lower face 53), where these three faces 430, 431, 432 together form a surface of revolution centered around a third central axis G3; being obviously clear that this surface of the third orifice 43 is smooth and devoid of any internal thread.

Referring to the section C-C of FIG. 8, the taper angle AC3 of the flared face 432 of the third orifice 43 is in the range of 40 degrees.

Referring to FIGS. 11A and 11B, the iliac anchoring screw 63, extending according to a main axis AV3 called screwing axis, has a threaded rod 631 extended by a head 630 having a spherical shaped bearing surface, where this bearing surface bears directly and polyaxially on the bearing face 431 of the third orifice 43.

Because of the shape of the bearing face 431 and of the flared face 432, the iliac anchoring screw 63 has, inside this third orifice 43, an angular displacement D3 in the range of 35 to 45 degrees between its two extreme positions, in other words the screwing axis AV3 of the iliac anchoring screw 63 can evolve inside a cone with an angle D3 centered on the third central axis G3.

More Specifically, this Third Central Axis G3 Satisfies the following Geometric Conditions:
- as shown in FIG. 2, the third central axis G3 has an angle AX3 with the vertical axis (Z) in the plane (Y, Z) comprised between −40 and −50 degrees, and in particular between −43 and −47 degrees, this angle AX3 being −45 degrees in the example of FIG. 2;
- as shown in FIG. 3, the third central axis G3 has an angle AY3 with the vertical axis (Z) in the plane (X, Z) comprised between −5 and +5 degrees, and in particular between −2 and +2 degrees, this angle AY3 being 0 degrees in the example of FIG. 3, so that this angle AY3 is not referenced;
- as shown in FIG. 4, the third central axis G3 has an angle AZ3 with the transverse axis (Y) in the plane (X, Y) comprised between −5 and +5 degrees, and in particular between −2 and +2 degrees, this angle AZ3 being 0 degrees in the example of FIG. 4, so that this angle AZ3 is not referenced.

Thus, both the first central axis G1 and the third central axis G3 extend in planes parallel to each other and parallel to the plane (Y, Z), as shown in FIGS. 3 and 4.

Referring to FIGS. 5 to 7, thanks to the orientations of the three central axes G1, G2, G3 and thanks to the geometric conformations of the three orifices 41, 42, 43, the three anchoring screws 61, 62, 63 may have, when in place, a particularly advantageous configuration with an arrangement of their screwing axes AV1, AV2, AV3 according to a three-orthogonal trihedron, where more specifically:
- as shown in FIG. 5, the screwing axis AV1 of the first sacral anchoring screw 61 is orthogonal to the screwing axis AV3 of the iliac anchoring screw 63;
- as shown in FIG. 7, the screwing axis AV1 of the first sacral anchoring screw 61 is orthogonal to the screwing axis AV2 of the second sacral anchoring screw 62; and
- as shown in FIGS. 6 and 7, the screwing axis AV2 of the second sacral anchoring screw 62 is orthogonal to the screwing axis AV3 of the iliac anchoring screw 63.

Of course, because of the angular displacements D1, D2, D3 of the anchoring screws 61, 62, 63 in the corresponding orifices 41, 42, 43, this configuration is not the only one possible.

Figure 14A:
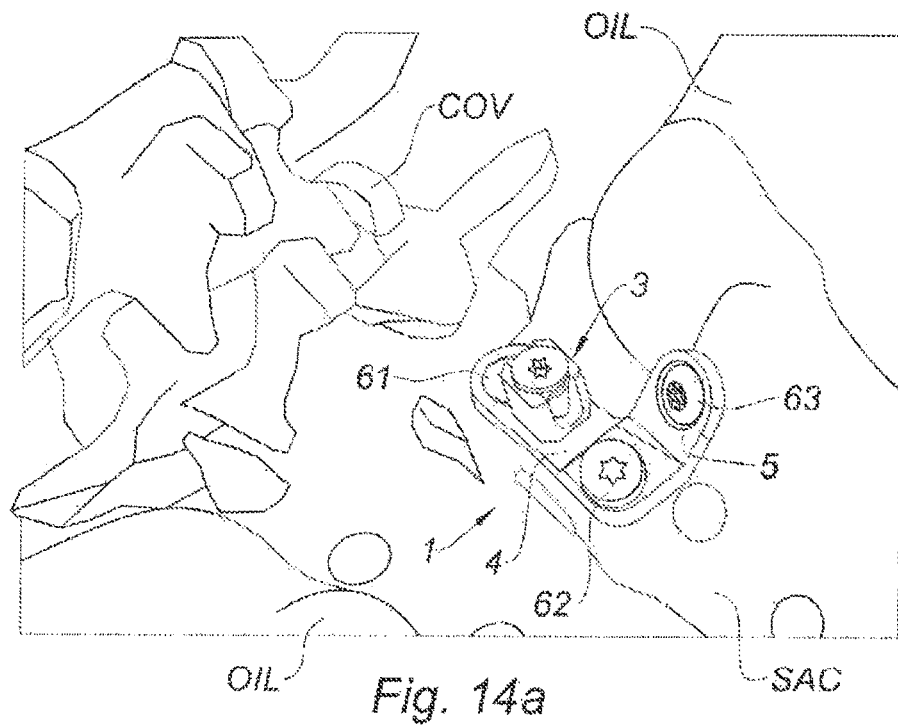
FIGS. 14a and 14b are schematic perspective views, according to two distinct angles of view, of the implant of FIG. 1 anchored on the sacrum and on the hip bone by means of the three anchoring screws.
Figure 14B:
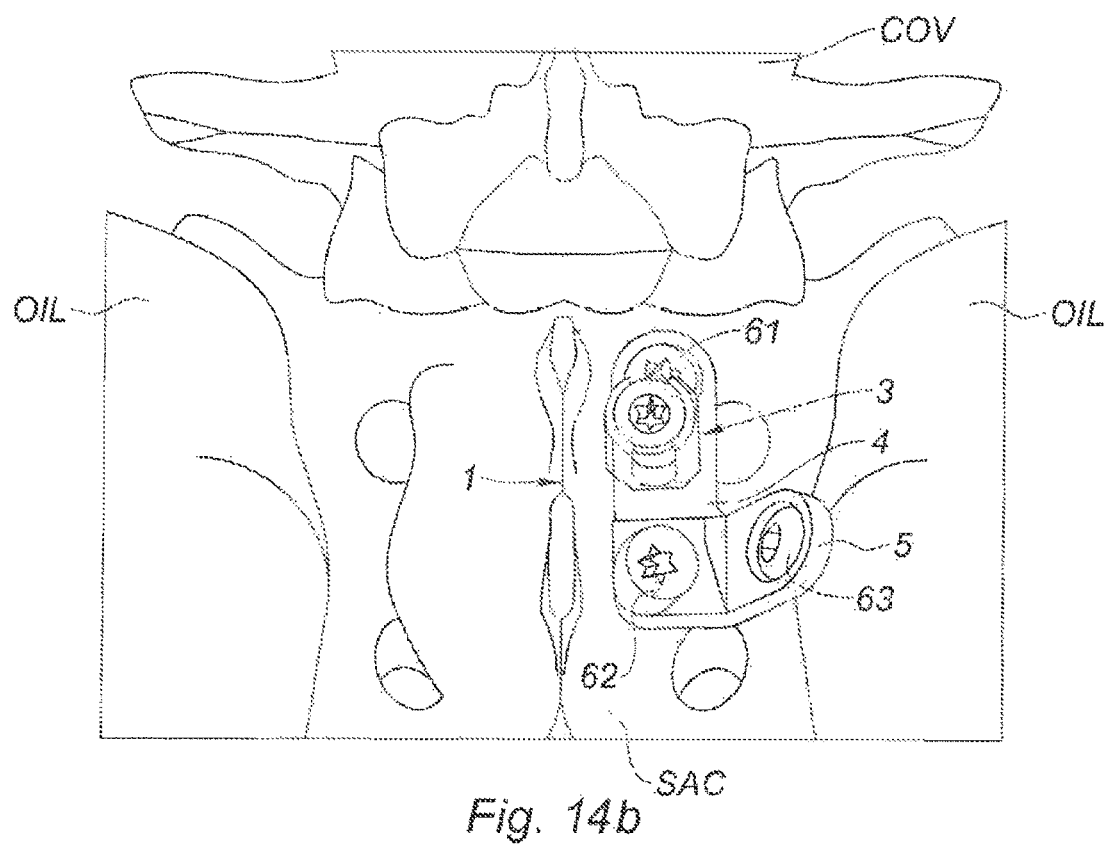

As illustrated in FIGS. 14a and 14b, when in place, the implant 1 is positioned on the sacrum SAC and the hip bone OIL, at the level of the sacroiliac joint (the articulation area between the sacrum. SAC and the hip bone OIL), with the main wall 4 pressed and screwed on the sacrum SAC by means of the two sacral anchoring screws 61, 62 and with the secondary wall 5 pressed and screwed on the hip bone OIL by means of the iliac anchoring screw 63.

Thanks to the invention, the anchoring screws 61, 62, 63 bear by their respective bearing surfaces on the bearing faces 411, 421, 431 of the three orifices 41, 42, 43, which enables, after screwing of the three anchoring screws 61, 62, 63 in the sacrum SAC and in the hip bone OIL, rotations of these bearing surfaces of the anchoring screws 61, 62, 63 on the bearing faces 411, 421, 431 in order to allow preserving the disjoint movements of the sacrum SAC and of the hip bone OIL which are possible thanks to the sacroiliac joint.

In addition, during the fixation of the implant 1, after selection of the setting site and selection of the orientations of the anchoring screws 61, 62, 63, only three screwing actions of the anchoring screws 61, 62, 63 are sufficient to ensure the final fixation of the implant 1, thereby allowing reducing the intervention time for setting such an implant

The invention claimed is:

1. A sacroiliac fixation implant for an intervertebral linking rod, said sacroiliac fixation implant comprising a one-piece anchoring component supporting a connecting element for the linking rod and provided with three orifices including a first orifice for the passage of a first sacral anchoring screw, a second orifice for the passage of a second sacral anchoring screw, and a third orifice for the passage of an iliac anchoring screw, wherein the anchoring component comprises:
   a main wall elongated according to a longitudinal direction and having a lower face and an upper face opposite to the lower face, as well as opposite longitudinal edges comprising a first longitudinal edge and a second longitudinal edge, wherein the first orifice is formed at a first end of said main wall and the second orifice is formed at a second end of said main wall, and wherein the connecting element is mounted protruding from and secured on the upper face of the main wall and is interposed between the first orifice and the second orifice; and
   a secondary wall protruding from the second longitudinal edge of the main wall at a level of its second end, so that the anchoring component has a general «L» shape, said secondary wall having a lower face and an upper face opposite to the lower face, wherein the third orifice is formed on said secondary wall;
   wherein each orifice is at least delimited internally and successively, from the upper face in the direction of the lower face of the concerned main wall or secondary wall, by an inlet face being a cylindrical or conical portion, extended by a bearing face being a spherical portion in turn extended by a flared face being a truncated-cone portion with a predefined taper angle and which widens as it gets closer to the lower face,
   wherein the inlet face, the bearing face and the flared face together form a smooth surface of revolution centered around a common central axis, including a first central axis associated to the first orifice, a second central axis associated to the second orifice and a third central axis associated to the third orifice,
   wherein the main wall has a thickened portion at a level of the second end and a less thick portion between the first end and the thickened portion, wherein the thickened portion forms a raised step with respect to the less thick portion and the second orifice is formed in the thickened portion, and wherein the first orifice is formed in the less thick portion and the connecting element is provided on the less thick portion;
   and wherein the orientations of the central axes of the three orifices and the taper angles of the flared faces of the three orifices are shaped so as to enable at least one arrangement of screwing axes of the three anchoring screws according to a three-orthogonal trihedron, with a screwing axis of the first sacral anchoring screw orthogonal to a screwing axis of the second sacral anchoring screw and to the screwing axis of the iliac anchoring screw, and with the screwing axis of the second sacral anchoring screw orthogonal to a screwing axis of the iliac anchoring screw.

2. The sacroiliac fixation implant according to claim 1, wherein the connecting element comprises a fastener cooperating with a tightening member for tightening the linking rod on said fastener, wherein said fastener is pivotally mounted on a ball joint secured to the anchoring component so that said fastener has three rotational degrees of freedom on said ball joint.

3. The sacroiliac fixation implant according to claim 2, wherein the fastener has a full movability, relative to the ball joint and to the main wall, inscribed within a cone centered on this ball joint and with an apex angle larger than or equal to 40 degrees.

4. The sacroiliac fixation implant according to claim 1, wherein the secondary wall is inclined upward with respect to the main wall with an inclination comprised between 30 and 60 degrees.

5. The sacroiliac fixation implant according to claim 1, comprising a first point to an intersection between the first central axis and a plane of the lower face of the main wall, a second point corresponding to an intersection between the second central axis and the plane of the lower face of the main wall, and a third point corresponding to an intersection between the third central axis and a plane of the lower face of the secondary wall,
   and comprising a first line passing through the first point and through the second point, and a second line passing through the third point and the second point, said first line and said second line intersect on the second point at an angle comprised between 100 and 120 degrees.

6. The sacroiliac fixation implant according to claim 1, comprising an orthonormal frame composed of:
   a longitudinal axis parallel to the longitudinal direction of the main wall and orientated from the second orifice toward the first orifice,
   a transverse axis orthogonal to the longitudinal axis wherein the longitudinal axis and the transverse axis define a transverse longitudinal plane parallel to the lower face of the main wall and wherein said transverse axis is orientated from the first longitudinal edge of the main wall toward the second longitudinal edge of the main wall, and
   a vertical axis orthogonal to the lower face of the main wall and orientated from the lower face of the main wall toward the upper face of the main wall,
   wherein the longitudinal axis and the vertical axis define a vertical longitudinal plane, and wherein the transverse axis and the vertical axis define a transverse vertical plane, and
   wherein at least one of the following geometric conditions is satisfied:
     the first central axis has an angle with the vertical axis in the transverse vertical plane comprised between +5 and +15 degrees;
     the first central axis has an angle with the vertical axis in the vertical longitudinal plane comprised between −5 and +5 degrees;
     the first central axis has an angle with the transverse axis in the transverse longitudinal plane comprised between −5 and +5 degrees.

7. The sacroiliac fixation implant according to claim 1, comprising an orthonormal frame composed of:

a longitudinal axis parallel to the longitudinal direction of the main wall and orientated from the second orifice toward the first orifice, a transverse axis orthogonal to the longitudinal axis wherein the longitudinal axis and the transverse axis define a main plane parallel to the lower face of the main wall and wherein said transverse axis is orientated from the first longitudinal edge of the main wall toward the second longitudinal edge of the main wall, and a vertical axis orthogonal to the lower face of the main wall and orientated from the lower face of the main wall toward the upper face of the main wall, wherein the longitudinal axis and the vertical axis define a vertical longitudinal plane, and wherein the transverse axis and the vertical axis define a transverse vertical plane, and wherein at least one of the following geometric conditions is satisfied:
the second central axis has an angle with the vertical axis in the transverse vertical plane comprised between −15 and −25 degrees;
the second central axis has an angle with the vertical axis in the vertical longitudinal plane comprised between −18 and −28 degrees;
the second central axis has an angle with the transverse axis in the transverse longitudinal plane comprised between +37 and +47 degrees.

8. The sacroiliac fixation implant according to claim 1, comprising an orthonormal frame composed of:
a longitudinal axis parallel to the longitudinal direction of the main wall and orientated from the second orifice toward the first orifice,
a transverse axis orthogonal to the longitudinal axis wherein the longitudinal axis and the transverse axis define a transverse longitudinal plane parallel to the lower face of the main wall and wherein said transverse axis is orientated from the first longitudinal edge of the main wall toward the second longitudinal edge of the main wall, and
a vertical axis orthogonal to the lower face of the main wall and orientated from the lower face of the main wall toward the upper face of the main wall,
wherein the longitudinal axis and the vertical axis define a vertical longitudinal plane, and wherein the transverse axis and the vertical axis define a transverse vertical plane, and
wherein at least one of the following geometric conditions is satisfied:
the third central axis has an angle with the vertical axis in the transverse vertical plane comprised between −40 and −50 degrees;
the third central axis has an angle with the vertical axis in the vertical longitudinal plane comprised between −5 and +5 degrees;
the third central axis has an angle with the transverse axis in the transverse longitudinal plane comprised between −5 and +5 degrees.

9. The sacroiliac fixation implant according to claim 1, wherein the main wall has, according to its longitudinal direction, a length comprised between 35 and 50 millimeter, a width considered between its first longitudinal edge and its second longitudinal edge comprised between 10 and 15 millimeter, and a thickness considered between its lower face and its upper face comprised between 2.5 and 4.5 millimeter.

10. The sacroiliac fixation implant according to claim 1, wherein the anchoring component has an overall height, considered according to a vertical axis orthogonal to the lower face of the main wall, comprised between 13 and 17 millimeter.

11. The sacroiliac fixation implant according to claim 1, wherein the truncated-cone shaped flared face of each orifice has a taper angle comprised between 20 and 50 degrees.

12. The sacroiliac fixation implant according to claim 1, wherein the less thick portion of the main wall has a thickness which is constant and smaller than a thickness of the thickened portion.

13. The sacroiliac fixation implant according to claim 1, wherein the secondary wall extends the thickened portion of the main wall transversely, according to a transverse direction orthogonal to the longitudinal direction of the main wall.

14. A sacroiliac fixation system for an intervertebral linking rod, said system comprising
a sacroiliac fixation implant according to claim 1, and
three anchoring screws comprising a first sacral anchoring screw engaged in the first orifice of the anchoring component and extending according to a screwing axis, a second anchoring screw engaged in the second orifice of the anchoring component and extending according to a screwing axis, and an iliac anchoring screw engaged in the third orifice of the anchoring component and extending according to a screwing axis,
wherein each anchoring screw has a threaded rod extended by a head having a spherical shaped bearing surface,
wherein said spherical shaped bearing surface bears directly and polyaxially on the bearing face of the corresponding orifice,
wherein the orientations of the central axes of the three orifices and the taper angles of the flared faces of the three orifices enable an arrangement of the screwing axes of the three anchoring screws according to a three-orthogonal trihedron, with the screwing axis of the first sacral anchoring screw orthogonal to the screwing axis of the second sacral anchoring screw and to the screwing axis of the iliac anchoring screw, and with the screwing axis of the second sacral anchoring screw orthogonal to the screwing axis of the iliac anchoring screw.

* * * * *